US005976099A

United States Patent [19]

Kellogg

[11] Patent Number: 5,976,099

[45] Date of Patent: Nov. 2, 1999

[54] METHOD AND APPARATUS TO MEDICALLY TREAT SOFT TISSUE DAMAGE LYMPHEDEMA OR EDEMA

[76] Inventor: Donald L. Kellogg, 115 Oakdale Dr., Aptos, Calif. 95003

[21] Appl. No.: 08/993,451

[22] Filed: Dec. 18, 1997

[51] Int. Cl.[6] .......... A61F 5/00

[52] U.S. Cl. .......... 602/23; 602/20; 602/9; 128/877

[58] Field of Search .......... 602/9, 13, 12, 602/20, 21, 22, 23, 19; 601/124, 125, 131, 133, 134, 135, 151; 128/877, 869, 882

[56] References Cited

U.S. PATENT DOCUMENTS

| | | | |
|---|---|---|---|
| 2,533,504 | 12/1950 | Poor . | |
| 2,669,165 | 1/1955 | Ferrier . | |
| 2,781,041 | 2/1957 | Weinberg . | |
| 2,943,859 | 7/1960 | Koski et al. . | |
| 3,173,420 | 3/1965 | Mazzoni et al. . | |
| 3,403,676 | 10/1968 | Gibbons | 602/8 |
| 3,454,010 | 7/1969 | Lilligren et al. . | |
| 3,459,179 | 8/1969 | Olesen | 601/134 |
| 3,548,819 | 12/1970 | Davis et al. . | |
| 3,561,435 | 2/1971 | Nicholson . | |
| 3,728,875 | 4/1973 | Hartigan et al. . | |
| 3,745,998 | 7/1973 | Rose | 602/13 |
| 3,845,769 | 11/1974 | Shaw . | |
| 3,862,629 | 1/1975 | Rotta . | |
| 3,885,554 | 5/1975 | Rockwell, Jr. . | |
| 3,901,225 | 8/1975 | Sconce | 602/13 |
| 3,942,518 | 3/1976 | Tenteris et al. . | |
| 3,975,929 | 8/1976 | Fregeolle . | |
| 4,013,069 | 3/1977 | Hasty . | |
| 4,030,488 | 6/1977 | Hasty . | |
| 4,180,065 | 12/1979 | Bowen . | |
| 4,320,746 | 3/1982 | Arkans et al. . | |
| 4,370,975 | 2/1983 | Wright . | |
| 4,374,518 | 2/1983 | Villanueva . | |
| 4,402,312 | 9/1983 | Villari et al. . | |
| 4,552,133 | 11/1985 | Kawaguchi . | |
| 4,583,522 | 4/1986 | Aronne . | |
| 4,773,397 | 9/1988 | Wright et al. . | |
| 4,862,879 | 9/1989 | Coombs | 602/13 |
| 4,922,893 | 5/1990 | Wright et al. . | |
| 4,938,208 | 7/1990 | Dye . | |
| 4,961,418 | 10/1990 | McLaurin-Smith . | |
| 5,025,781 | 6/1991 | Ferrari . | |
| 5,063,910 | 11/1991 | Cartier . | |
| 5,108,426 | 4/1992 | Biro et al. . | |
| 5,109,832 | 5/1992 | Proctor et al. . | |
| 5,117,812 | 6/1992 | McWhorter . | |
| 5,171,211 | 12/1992 | Deasy, Jr. . | |

(List continued on next page.)

*Primary Examiner*—Richard J. Apley
*Assistant Examiner*—Justine R. Yu
*Attorney, Agent, or Firm*—James J. Leary; Patrick T. Reilly

[57] ABSTRACT

A method and apparatus for the alleviation of an undesirable fluid accumulation in a body area of a patient is provided. The apparatus, or static reaction system has enclosure containing a multiplicity of particles that are pressed against the body area. The shape of the enclosure and the physical qualities of the particles affect the suitability of specific versions of the invention to particular conditions and body areas. Pockets are included in some versions of the enclosure to capture and isolate subsets of the multiplicity of particles. An optional directional flow pattern feature is established by the orientation, sizes and shapes of the optional pockets and thereby affects the rate at which the fluid accumulation is reduced. Lightweight and flexible materials are used to manufacture various comfortable, transportable and storable models of the invention. The enclosure is optionally constructed with low friction, porous and breathing fabrics and materials to improve patient comfort and patient compliance. The enclosure is pressed, held and/or forced against a selected body area by means of a detachable compression cover, a pneumatic pack, compressive bandaging or wrapping, and made with velcro stretch fabric and/or with velcro strapping or other suitable means. Certain versions of the invention are applied by a capable and competently trained patient and with reduced need of constant professional supervision.

35 Claims, 8 Drawing Sheets

U.S. PATENT DOCUMENTS

| | | | |
|---|---|---|---|
| 5,172,689 | 12/1992 | Wright . | |
| 5,228,142 | 7/1993 | Yoswein-McGreen . | |
| 5,233,974 | 8/1993 | Senoue et al. . | |
| 5,245,990 | 9/1993 | Bertinin . | |
| 5,257,956 | 11/1993 | Ewen . | |
| 5,310,400 | 5/1994 | Rogers et al. . | |
| 5,618,263 | 4/1997 | Alivizatos | 602/6 |
| 5,718,669 | 2/1998 | Marble | 605/5 |
| 5,728,055 | 3/1998 | Sebastian | 602/19 |

METHOD AND APPARATUS TO MEDICALLY TREAT SOFT TISSUE DAMAGE LYMPHEDEMA OR EDEMA

FIELD OF THE INVENTION

The present invention relates to medical techniques and devices used to treat soft tissue inflammation, damage, edema and/or lymphedema. The present invention relates more particularly to the application of physical pressure against the swollen tissue of a body area for the purpose of reducing an undesirable internal accumulation of interstitial fluid, while minimizing patient discomfort and thereby encouraging patient compliance in treatment

BACKGROUND OF THE INVENTION

The lymphatic system is organized like the blood system in that it includes a system of numerous tiny vessels connected to a network of larger vessels, and through which system and network a liquid medium containing solutes and particulates is transferred. A healthy lymphatic system continuously drains lymphatic fluid, consisting of a mixture of lymph, water, proteins and other matter, away from various interstitial areas of the body and back into the blood system. Lymph is the clear, liquid medium or solvent of the lymphatic system.

The lymph fluid is pumped through the lymphatic system and away from various body areas by both the action of adjacent muscle tissue and the contraction of the larger lymphatic vessels. Foreign matter is filtered out of the lymph fluid as the fluid passes through bundles of lymph nodes during its course through the lymphatic system. The lymph nodes also monitor the contents of the lymph fluid to determine if any appropriate immune reactions should be initiated by the host's immune system. The lymph is then transferred back into the blood system after this filtration.

Lymphedema is a deficiency, blocking or dysfunction of the lymphatic system that limits the flow of lymph fluid from a body area. The most frequent causes of lymphedema include primary insufficiency, traumatic accidents, chronic venous diseases, radiation therapy of the lymph nodes, prostate operations, mastectomies, amputations and other surgical operations. Lymphedema most typically occurs in arms and legs, but most other body areas can become lymphedemic, such as the genitals and the trunk of the body.

Lymphedema and edema can cause reduction in mobility, pain, embarrassment and serious emotional depression. Rapid swelling, such as caused by radiation therapy or a surgical operation, can be especially painful as the body tissue is effectively being torn apart by the fluid pressure. The World Health Organization recently estimated that approximately 500 million people currently suffer from some form of lymphedema.

Individual cases of lymphedema are typically diagnosed as belonging to either a primary or a secondary class. Primary lymphedema is a condition where the lymphatic system is chronically or acutely overwhelmed by the volume of lymphatic fluid to be evacuated. Chronic primary lymphedema is often a genetically determined condition. Acute primary lymphedema, and edema, can be caused by an injury or trauma where the lymph system is properly functioning but is temporarily overwhelmed. Swelling and/or edema caused by burns, sprains and other injuries are typically alleviated after a few days or weeks in a patient in generally good health. However, even temporary swelling can be painful to the patient and can result in fibrosis.

Secondary lymphedema is typically presents as a relatively sudden cessation or deep reduction of the functionality of a portion of the lymphatic system. The most frequently occurring causes of secondary lymphedema include radiation therapy, mastectomies, amputations and other surgical operations.

Regardless of cause or class, a significant limitation or attenuation of the necessary progress of lymphatic fluid through the lymphatic system may result in a concentration or swelling of the protein bearing lymph fluid in the interstitial area of the soft tissue of an affected limb or body region. Chronic lymphedema more often results in severe and even life threatening consequences than acute edemas.

Any sustained accumulation of proteins delivered to the body tissue by the blood capillaries, and not removed by the lymphatic system, will cause a swelling of fluid in the interstitial areas of the body tissues. The oxygenation of adjacent tissue is thereby reduced and the healing process is retarded. A localized accumulation of proteins further compounds this situation by directly stimulating chronic inflammation. Chronic inflammation usually results in the formation and dilation of additional capillaries. These additional blood vessels deliver undesirable excess heat to the swollen area. This inopportune heating of the protein rich interstitial fluid increases the incidence and virulence of opportunistic bacteriological infections.

Conventional treatment techniques for lymphedema include the use of benzo-pyrene drugs, massage therapy, physical exercise, compression bandages and compression garments. Treatment strategies that apply physical pressure to a swollen, edemic or lymphedemic body area can be divided into those which provide intermittent forced compression and those which maintain a relatively constant pressure over time. Looking first at intermittent forced compression devices, Ferrari, in U.S. Pat. No. 5,025,781, discloses an inflatable cuff that is alternately inflated and deflated to deliver a uniform blanket compression against the circumference of a swollen limb. This action may, however, exacerbate the patient's condition by collapsing blood vessels, increasing leakage into the interstitial areas and obstructing lymphatic outflow.

Bertinin, in U.S. Pat. No. 5,245,990, describes an inflatable sheath which consists of a number of inflatable tubes. The tubes are inflated and deflated in a sequence starting from the most distal and ending at the most proximal. Inventor Bertinin intends to supply a wave-like massage to the swollen limb. Bertinin's method of timed and sequential inflation and deflation is similar to the invention of Ferrari in that a uniform blanket pressure is exerted against the swollen tissue at any particular moment. This blanket pressure is reported to typically be ineffective by medical practitioners of the art. In addition, compressive devices which include pneumatic pumps can cause damage to the health of the patient and must typically by applied by a trained medical practitioner.

Schneider packs, an alternative prior art example, are used to apply constant pressure to a body part Schneider packs consist of small packs of randomly placed pieces of high density foam bound within a tubular cloth pouch or tube. Schneider packs are incorporated into bandaging and usually can not be attached by the patient without assistance.

Improvements in treating lymphedema were recently made by Tony Reid, M.D. and Applicant in a previous invention. This previous invention of Reid and Applicant, and marketed as a Reid Sleeve, includes a sheet of convoluted plastic foam and a means to push the extending elements, or fingers, of the convoluted foam sheet against a swollen body part. The foam fingers are prearranged neatly on the foam sheet in well ordered rows and columns, and create a grid pattern of high and low pressure areas when pressed against the patient's body area. The convoluted foam sheet is encased in an inner lining of a spandex material and an outer lining of relatively heavy nylon fabric. Adjustable velcro straps and matching D ring straps are sewn into the outer lining, by which means the convoluted plastic foam sheet is secured and pressed against and/or around a body part. In application, a medical practitioner can use a pressure gauge while applying this earlier invention of Reid and Applicant to cinch the velcro straps to a particular pressure point or to within a preferred pressure range.

The use of a solid convoluted foam sheet adds, in light of the present invention, unnecessarily to the weight of the device of Reid and Applicant. Furthermore, the use of a heavy nylon fabric in the outer lining of the device of Reid and Applicant limits the patient's range of motion and wearing comfort. A typical Reid Sleeve arm design weighs over three pounds. In addition, the direct attachment of the velcro strapping and matching D ring straps to the heavy nylon fabric reduce the uniformity of pressure exerted by individual fingers across the total circumference of a limb or body part.

The design of the invention of Reid and Applicant is not configurable to apply pressure to a combination of a limb and an adjacent body area (e.g. leg and groin, leg and hip, arm and shoulder, and etc.) with a single assembly device. The employment in the Reid Sleeve of heavy nylon fabric also limits the adjustability of a particular sleeve to a small range of arm circumferences or arm sizes.

There has been a long felt need in the medical treatment of lymphedema, edema and other soft tissue swelling for a more effective, widely applicable, comfortable, easily transportable, and more patient manageable device and method of use.

SUMMARY OF THE PRESENT INVENTION

It is an object of the present invention to provide a method and an apparatus to reduce undesirable fluid accumulations in a body area of a patient. The method of the present invention attains this object by compressing a plurality or a multiplicity of particles against a swollen body area and thereby creating a network of relatively narrow low pressure channels and a relatively large high pressure surface area where the network of channels intersects the high pressure surface area, and thereby increases the rate of drainage of the interstitial fluid through the channels and from the affected body area. The evacuating fluid may be driven out of the body area solely through the channels and/or through introduction into the lymphatic system.

The invented apparatus, or static reaction system, includes an enclosure of particles to organize the particles and a compressive means to press the enclosure of particles against the body of a patient. The enclosure may contain the particles. Certain preferred embodiments of the present invention include a compression cover as compressive means to press the enclosure of particles against the patient's body. Certain alternate preferred embodiments of the invented system include a pneumatic jacket and a pneumatic pressure source as compressive means.

The enclosure of particles, or enclosure, may organize a set of particles on a layer of material or a sheet of fabric, or contain the set of particles between two encasing layers of material or sheets of fabric. This set of particles includes a quantity of individual particles which exhibit uniform or non-uniform shapes, sizes, densities and/or resiliencies. In certain alternate preferred embodiments of the present invention glues or adherents are optionally used to affix some or all of the particles to one or more organizing or encasing layers of material or fabric sheets of the enclosure. The enclosure presents a compressing surface area which is compressed against the patient's swollen body area. The encasing layers or sheets are optionally constructed from a group of fabrics and materials to include cotton/lycra, spandex, cotton, lycra, four way stretch fabrics, easily stretched stitching, low friction fabrics, porous or breathing fabrics, absorbent cloth and other suitable materials known in the art.

The application of the present invention against a swollen area of a patient's body creates a plurality or a multiplicity of relatively large high pressure areas and an intersecting network of narrow, lower pressure channels. The pressure differential thereby created drives the interstitial fluid from the high pressure areas and into the network of channels. The network of channels leads the interstitial fluid into the lymphatic system and/or out of and away from the body area which is under compression by the present invention. The interstitial fluid is thus transferred, in certain preferred embodiments of the invented system, from a part of the body where the lymphatic system is either damaged, blocked or merely overwhelmed, and into other body areas where healthy lymphatic tissue is available and functioning. The interstitial fluid is then accepted into the lymphatic system and returned after filtering to the blood system.

In certain preferred embodiments of the present invention the enclosure further includes individual pockets. These pockets temporarily or permanently isolate and contain groups of particles, or subsets, of the set of particles of the enclosure. Each pocket contains one or more particles. The pockets may be formed by stitching, connecting or joining the encasing layers together, or by other suitable means known in the art, so as to capture and isolate separate subsets of particles into the individual pockets. Stretchable fabrics, elastic threads and/or stretch stitching patterns may be used in creating the pockets and to allow the pockets to stretch easily throughout a patient's range of motion.

The shapes, sizes and orientations of the pockets can influence the speed with which fluid is dispersed within the patient, and thereby can contribute to the effectiveness of the present invention. The orientation of the pockets to each other and to the body of the patient can also affect the rate at which fluid is relieved from a swollen area. This optional and inventive feature of the present invention provides an established pocket or a pattern of pockets within an enclosure is referred to as a directional flow pattern. Certain preferred embodiments of the present invention include this feature of the directional flow pattern, which requires the establishment of one or more pockets, and optionally includes the intentional sizing and shaping, and orientation of the pockets to the sizes, shapes and relative positions of the other pockets, for the purpose of enhancing the alleviation of lymphedema, edema or swelling and/or the pain caused by the swelling of soft tissue.

The enclosures of devices made in accordance with the method of the present invention are manufactured and applied in various forms such as tubular tapered cones, tubular shapes, flat or plump round pillow shapes, quadrilateral pillow shapes, reversible shapes and/or limb specific shapes. Certain preferred embodiments of the present invention are optionally shaped to encourage fluid drainage from both a body limb and/or one or more adjacent body parts or areas, to include such combinations as hand-arm-shoulder embodiments or foot-leg-hip embodiments, or shoulder and breast embodiments.

Certain alternate preferred embodiments are specifically shaped for application against a patient's groin, torso and/or trunk.

In application, the enclosure is held, pressed or forced against an area of a patient's body. Pressure or force is optionally exerted against the selected body area by means of a compression cover which may optionally include a pneumatic pump and a pneumatic jacket or jackets, or bandages, or compression wrappings. Certain of the preferred embodiments employing bandages or compression wrappings further include velcro stretch fabric, velcro strapping or other suitable means known in the art.

Certain preferred embodiments of the present invention include an enclosure that is constructed of light cotton/lycra fabric, sewn together with cotton and/or elastic thread and into hollow tubular cone shapes designed to fit around a leg or arm. Many of these preferred embodiments include a directional flow pattern. The directional flow pattern feature is formed, in certain of these preferred embodiments, by sewing the cotton/lycra pockets together with the cotton and/or elastic thread to create individual pockets. The pockets isolate groups of high resiliency plastic foam particles into particular shapes, such as chevrons or long rectangles. The pockets are sized, shaped and oriented in a pattern that directly increases the rate of drainage of the interstitial fluid.

Preferred embodiments of the present invention designed for limb treatments, and comprising directional flow patterns which include a series of chevron shaped pockets of two inch thickness, with the point of the chevron oriented proximal, and where the pattern of chevrons starts distal and inside the limb and proceeds to rotate to the outside and proximal directions of the limb, have been used to good effect in treating patients with secondary lymphedema in the treated limb. A series of chevron shaped pockets has proven to be effective in transferring a concentration of interstitial fluid from an area of the body where the lymphatic system is damaged, to an alternate body area from where the lymphatic system can and does accept the transferred interstitial fluid.

Alternatively, primary lymphedema has been treated with enclosures sewn to provide directional flow patterns comprising pockets filled with high resiliency foam plastic particles, where the pockets are shaped as relatively long and thin rectangles and the length dimension is oriented to along a roughly distal/proximal axis of the treated limb. Directional flow patterns including long thin rectangles have been effectively used to increase the rate of interstitial fluid intake a portion of the lymphatic system located within the body area against which the static reaction system is directly applied.

Preferred embodiments intended for an application about a patient's neck may be shaped as a series of long, thin rectangular pockets where the longer dimension of the pockets is oriented around the circumference of the neck, rather than along a distal/proximal axis.

Certain preferred embodiments of the present invention intentionally include mixtures of particles of varying characteristics, such as chemical composition, resiliency, density, shape and/or size. The employment of mixtures of non-uniform particles in certain preferred embodiments of the present invention has been shown to be effective in the treatment of several patients.

Certain preferred embodiments of the method of the present invention include the monitoring of the magnitude of pressure with which the compression cover and enclosure exert against a body area. This optional applied compressive pressure monitoring capability, which can be continual, occasional or intermittent, permits a medical practitioner an increased confidence that the pressure applied against the body part is within a desirable range. Certain alternate preferred embodiments of the method of the present invention allow the medical practitioner to periodically mark the compression cover with an adjustable element so as to allow the patient to safely self administer, compress and attach these preferred embodiments under less frequent direct medical supervision.

The sets of particles of the enclosures of various preferred embodiments of the present invention may include specific uniform and non-uniform combinations of shapes, grades, densities, sizes and resiliencies of particles which are particularly appropriate for application with particular body areas, such as a leg or a groin area Certain of those preferred embodiments configured for combinational body part application, e.g. a leg and groin design, an arm and shoulder design or a shoulder and breast combination, optionally include sections of the enclosure where different and specially selected combinations of particles are selected to better meet the needs of the different body areas of intended application. For example, an arm and shoulder embodiment might include a first arm section of the enclosure containing a combination of particles especially selected for application against an arm, and a second section of the same enclosure where the second shoulder section contains a different combination of particles which are especially selected for application against a shoulder.

The use of light weight particles in certain preferred embodiments of the present invention allows for the provision a light weight, easily transportable and storable apparatus. The use of light weight, compressible particles in combination with the use of flexible and light weight fabric in the manufacture of the enclosures and compressive means of certain alternate preferred embodiments of the present invention further supports the provision of an easily transportable and storable apparatus. A typical embodiment of the present invention made of light weight fabrics and particles, and capable of treating an entire arm of an adult patient, weighs under ten ounces and can be rolled up for compact storage and transport.

Certain preferred embodiments of the invented system allow for the interleaved application of combinations of embodiments of the present system in a variety of modalities within the treatment regime of a specific patient. This clinical feature of method of the present invention empowers a medical practitioner or care giver to optionally and flexibly vary the treatment regimes of two or more preferred embodiments of the invented system to improve the therapeutic quality of care delivered to an individual patient. A particular patient might respond best to, for example, short periods of treatment with a pneumatic compressive means, in concert with prolonged wearing of an alternate preferred embodiment of the invented comprising a compressive cover.

DETAILED DESCRIPTION OF PREFERRED EMBODIMENTS

The following disclosure is illustrative only and not limiting. Various and numerous alternate embodiments of the present invention are made obvious to one skilled in the art in view of this disclosure.

Figure 1:
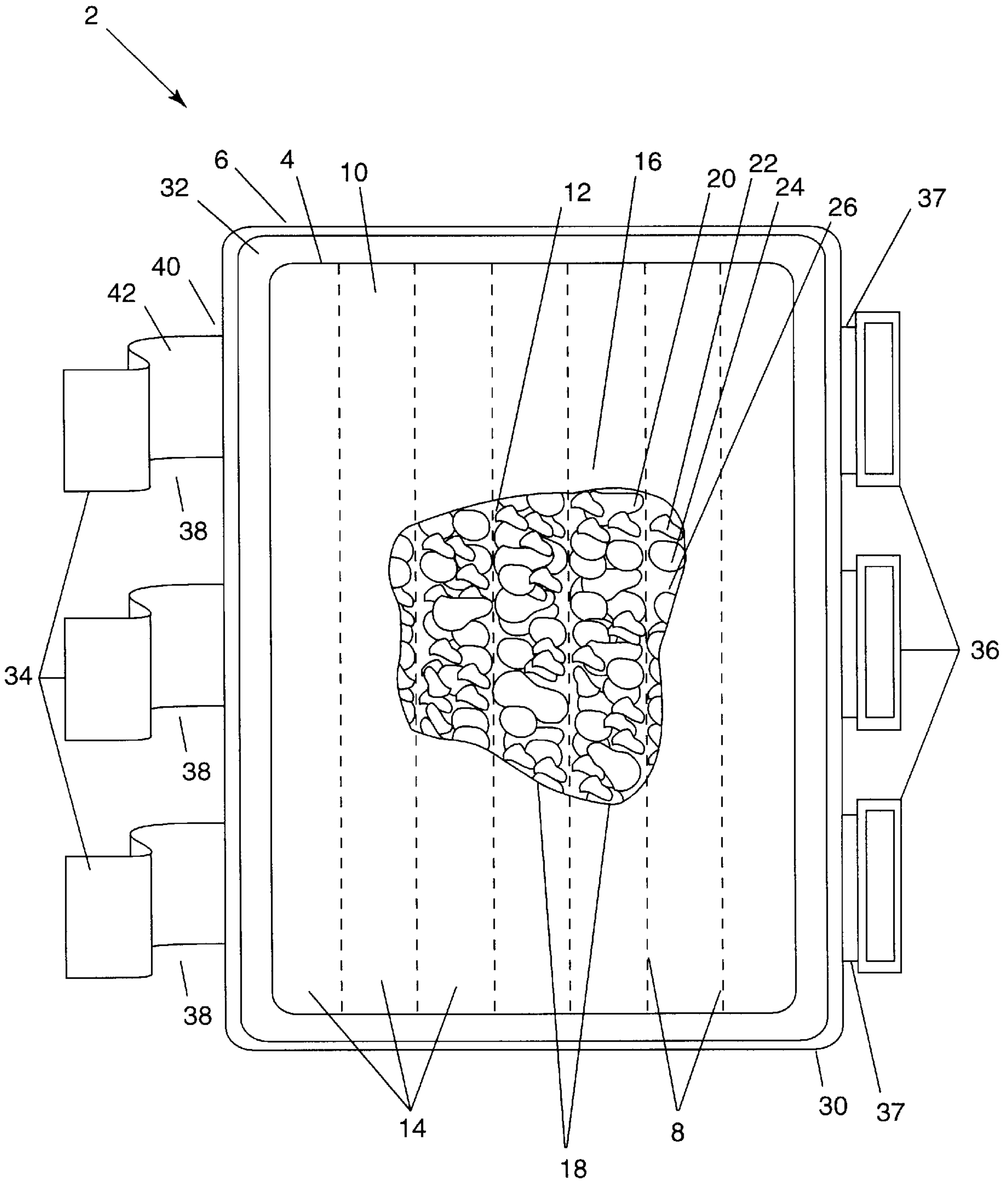
FIG. 1 illustrates a preferred embodiment of the present invention including a static reaction system with a directional flow pattern and a quadrilateral enclosure. A cut-away view depicts the inside and the contents of the enclosure. The directional flow pattern is created by sewing a plurality of chevron shaped pockets pointing along a common axis.

Referring first to FIG. 1, a preferred embodiment of the present invention, which includes an essentially quadrilaterally shaped static reaction system 2 with a directional flow pattern, is depicted. The invented system 2 includes an enclosure 4 and a compression cover 6. The enclosure 4 includes the directional flow feature, or aspect, of the invented system 2 wherein a plurality of pockets 14 contain a set of particles 16. The set of particles 16 includes a multiplicity of particles, or particle types, 20, 22, 24, as shown in the cut-away view of the enclosure 4. The directional flow aspect of the preferred embodiment 2 of FIG. 1 is realized by the establishment of the pockets 14, where the pockets 14 are shaped, sized and oriented to improve the evacuation of interstitial fluid from a particular body area. The enclosure 4 has a ten inch by ten inch surface area and employs a stitching 8, an inner fabric sheet 10 and an outer fabric sheet 12 to contain the set of particles 16. The set of particles 16 optionally includes one or more uniform or non-uniform individual particles, or particle types 20, 22, 24. The set of particles 16 is divided into a one or more subsets of particles 18. Each subset of particles 18 is temporarily or permanently contained in a separate pocket 14 and optionally includes one or more individual particles 20, 22, 24 of the set of particles 16. The stitching 8 defines the shape, size and orientation of each of the pockets 14 and sews the inner and outer sheets 10 and 12 together, and thereby establishes directional flow within the enclosure 4. Certain alternate preferred embodiments of the present invention use other suitable materials and techniques to establish the optional and invented directional flow feature.

The particles types 20, 22 and 24 are optionally made of compressible, high resiliency, low density, open cell plastic foam or other suitable material known in the art. The particle types 20, 22 and 24 are of either uniform or non-uniform size, shape, resiliency, density. The use of specific mixtures of the particle types 20, 22, 24 of varying shapes sizes, densities and resiliencies have yielded positive results in recent applications. Particle types 20, 22, 24 made of high resiliency, low density foam plastic, such as 100% shredded polyurethane foam of medical grade 100% virgin, California Registry Number 25506 is a particular material that have been successfully used in recent trials. Other suitable materials known in the art are used in the composition of the particle types 20, 22, 24 in various alternate preferred embodiments of the invented system.

The particle types 20, 22, 24 can be made by grinding a solid sheet of certain kinds of plastic foam sheets through an Andrew grinder. A mixtures of sizes and shapes of the particle types 20, 22, 24 can be produced by setting an Andrew grinder for a specified maximum size, for example ½ inch rounds, and feeding a plastic foam sheet or sheets, into the input stage of the grinder. Where a smaller maximum size of particles is required, for example ¼ cubic inch and less, a sieve is used to isolate the particle types 20, 22, 24 which are that size or smaller. Other suitable manufacturing techniques known in the art for making compressible high resiliency particles are employed in various alternate preferred embodiments in the production of particle types 20, 22, 24.

Certain alternate preferred embodiments of the invented system include other suitable high resiliency materials in the manufacture of the particle types 20, 22 and 24. Certain alternate preferred embodiments employ other techniques known in the art for manufacturing foam or plastic foam particles within a specified and required size range.

The specific variance of the physical qualities of the particle types 20, 22, 24 may be optionally selected in relationship to the expected application of the invented system 2. Applications on arms are well met with a mixture of particle types 20, 22, 24 of plastic foam material of ½ inch cubic size and lower, and with high resiliency ratings, or HR, of HR 11, HR 23 and HR 27. A mixture of particle types 20, 22, 24 of plastic foam material within the same size range but with HR ratings of HR 27, HR 35 and HR 40 are well used in leg applications. For groin applications, smaller particle types 20, 22, 24 of a size range of ¼ cubic inch and smaller in a mixture of HR 11, HR 23 and HR 27 are advised.

The inner and outer sheets 10, 12 are stitched or molded together or otherwise joined together to enclose the particle types 20, 22 and 24. Please note that the inner and outer sheets 10, 12 may be formed of one contiguous sheet folded over. The inner fabric sheet 10 is placed directly against the swollen tissue of the patient. The inner and outer sheets 10 and 12 may be made of cotton, nylon, spandex or other suitable materials known in the art. The stitching 8 is made of cotton, nylon, stretch stitch thread or other suitable material known in the art. Various alternate preferred embodiments of the present invention form the pockets 14 with and without the stitching 8 and/or with other suitable pocket forming means known in the art.

An adhesive 26 is optionally used to affix the particle types 20, 22 and 24 to either of the inner or outer sheet 10 or 12. Alternate preferred embodiments of the present invention employ neither an adhesive 26 nor any other means of affixing any of particle types 20, 22, 24 to either the inner or the outer sheet 10 or 12.

Preferred embodiments of the present invention which include pockets 14 shaped as long and relatively thin rectangles are preferred in treatment applications of trauma, soft tissue damage and primary lymphedema. Various other pocket shapes and sizes are effectively used in treatments of trauma, soft tissue damage and primary lymphedema.

Figure 2:
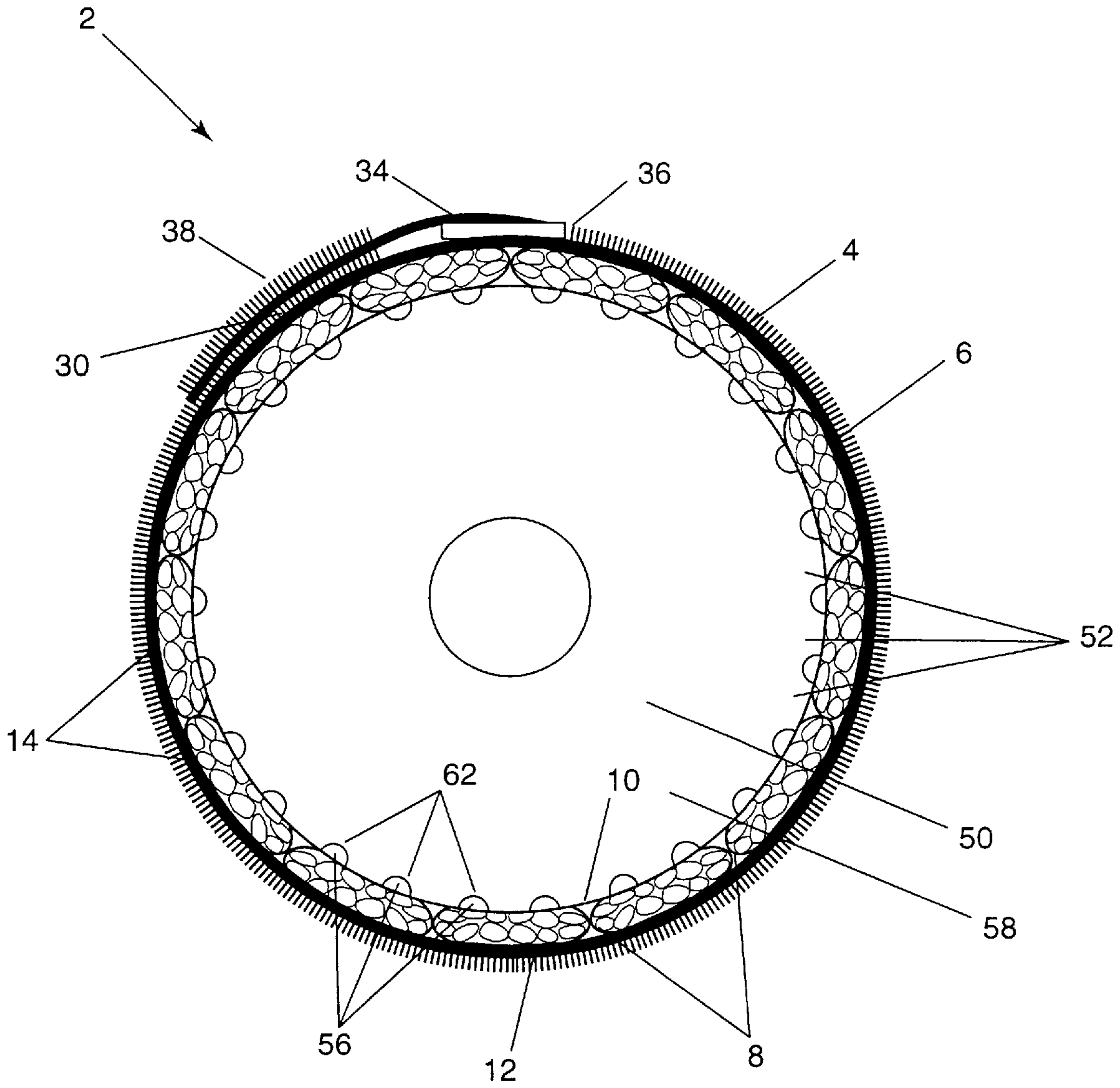
FIG. 2 is a cross sectional view of a preferred embodiment of the static reaction system similar in construction to the system of FIG. 1 applied around a limb of a patient.
Figure 3:
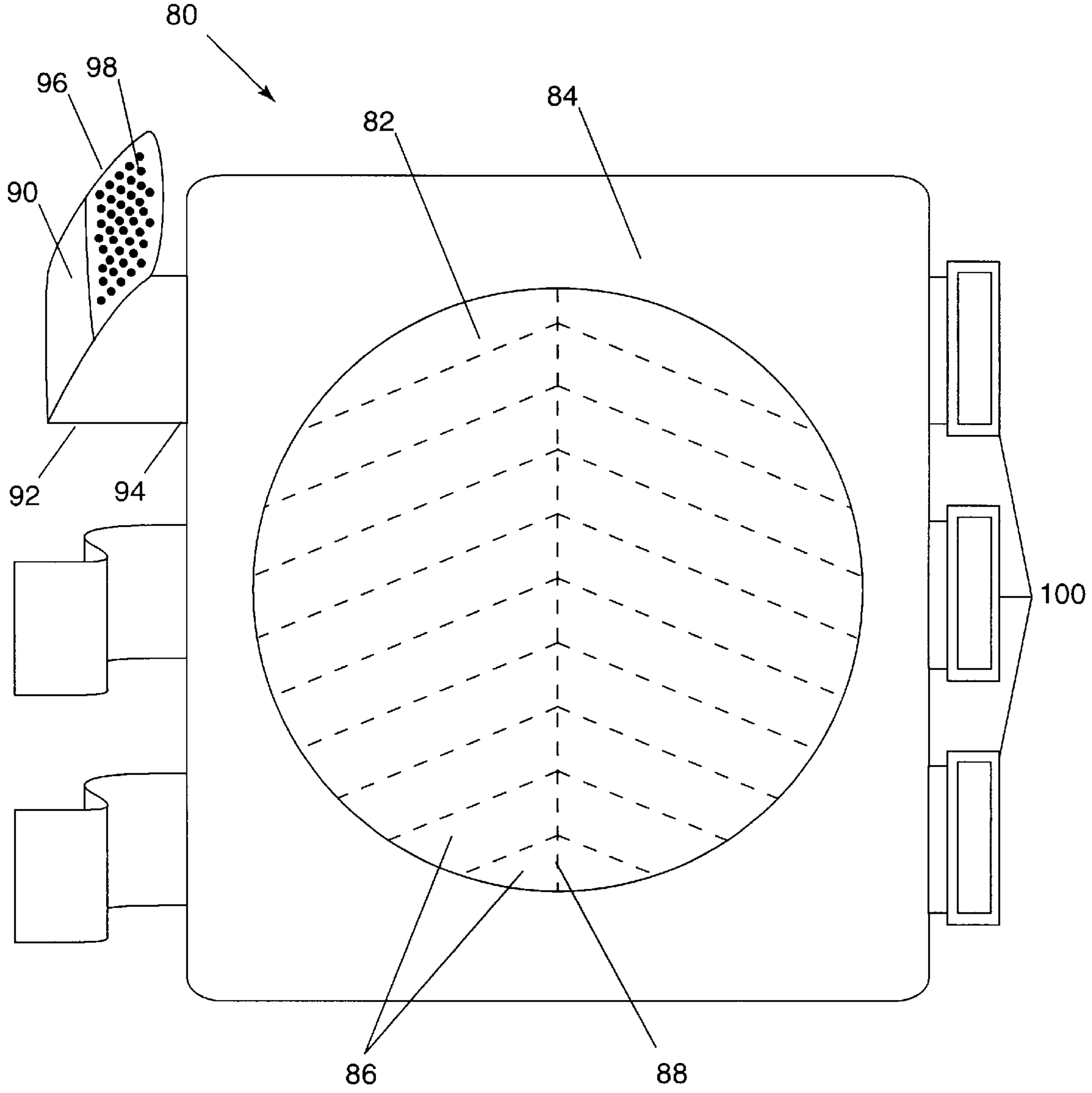
FIG. 3 discloses a static reaction system with a directional flow pattern and including a circular enclosure. The directional flow pattern is created by sewing a plurality of particle containing chevron shaped pockets pointing along a common axis.

The compression cover 6 provides the compressive means of the preferred embodiment of the invented system 2 of FIG. 1 and has a slightly larger surface area than the enclosure 4. The compression cover 6 includes a backing 30, as shown in FIG. 2, of loop-side velcro fabric (as seen in FIGS. 2 and 3), an internal lining 32, a plurality of straps 34, a number of fabric links 37 and a plurality of single looped rings 36. The stitching 8 attaches the lining 32, the straps 34, the fabric links 37 and the rings 36 to the velcro fabric 30. The lining 32 may be optionally made of cotton, nylon, nylon webbing, spandex or other suitable material. The rings 36 are made of metal, plastic or other suitable material. In certain alternate preferred embodiments the backing 30 may be made of cotton, nylon, nylon webbing, spandex or other suitable material exclusively or in combination with velcro fabric backing loop-side or hook-side fabric.

The use of lightweight and flexible materials in certain preferred embodiments of the invented system provides easily compressible, storable and/or transportable embodiments of the present invention. Furthermore, the use of flexible and light weight materials increases range of motion and patient comfort and thereby supports patient compliance.

Compression cover 6 is not attached to enclosure 4 but rather is separately held in place around the enclosure 4 and a body part by means of adjustable length straps 34, rings 36 and velcro fabric 30. This configuration of the preferred embodiment of the present invention 2 of FIG. 1 permits a range of fitting of the compression cover 6 and the enclosure 4 about varying sizes and diameters of body areas and limbs. This inventive feature of the present invention broadens the utility of certain embodiments of the present invention for treatment of patients of varying sizes and with individually fluctuating, and hopefully decreasing, swelling.

In addition, the optional separateness of the enclosure 4 and the compression cover 6 of the preferred embodiment of the present invention 2 of FIG. 1 allows the enclosure 4 and compression cover 6 to be washed and maintained separately.

Straps 34 are two inches wide and are individually attached by the stitching 8 at three inch intervals to loop-side velcro stretch fabric 30 and lining 32. Each strap 34 comprises a two inch wide and six to forty inch long band of hook-side velcro stretch fabric 38, a first end 40 and a second end 42. First end 40 is sewn with the stitching 8 to velcro fabric 30 and lining 32. Each second end 42 is passed through a single looped ring 36, where second end 42 is the doubled back and second end 42 is attached somewhere onto loop-side velcro fabric 30. The plurality of single loop rings 36 are wide enough for a strap 34 to flatly pass through rings 36. Single looped rings 36 are bound by fabric links 37 at three inch intervals, where the stitching 8 affixes fabric links 37 to velcro fabric 30 and lining 32.

In operation, the preferred embodiment of the invented system 2 of FIG. 1 is located against or around a body area. The enclosure 4 is placed against a body area and oriented so that the longer length dimension of the pockets 14 are positioned parallel to an axis passing from distal to proximal through the body area. The compression cover 6 is then placed over the enclosure 4 where the enclosure 4 is thereby sandwiched between the body part and the compression cover 6.

Referring now to FIG. 2, a cross sectional view of the static reaction system 2 with a directional flow pattern similar to that of FIG. 1 is shown as applied against a leg 50 of a patient. The compression cover 6 presses and holds the enclosure 4 against the leg 50. Each strap 34 passes through a single looped ring 36 and double backs toward the backing 30 of velcro loop-side fabric, where the hook-side velcro stretch fabric 38 of each strap 34 is attached to the backing 30 of velcro loop-side fabric of the compression cover 6. By this means and method a compressive force is adjustably imparted to the enclosure 4 and about the leg 50. The pressure of the particle types 20, 22 and 24 contained in the pockets 14 of the enclosure 4 is exerted against the leg 50 and creates the high pressure areas 52 in the leg 50. The interstitial fluid 56 contained within the soft tissue 58 is thereby forced away from the high pressure areas 52 and into the narrow channels 62.

FIG. 2 clearly shows that the selection of soft, pliant and flexible materials in the construction of the preferred embodiment of the present invention 2 allows compressive force to be delivered around a full 360 degree circumference of the leg 50 of the patient. This feature of the present invention 2 allows for an improved application of compressive pressure over the prior art in many clinical applications.

Another advantage of the present invention 2 over the prior art is created by the use of a relatively large surface area of velcro loop-side fabric in the backing 30 of the compression cover 6 for the attachment of the plurality of the hook-side velcro stretch fabric elements 38 of the straps 34. This access to a large area of the compression cover 6 for attachment by the hook-side velcro stretch elements 38 of the straps 34 allows a patient to be more comfortably fitted with the invented system 2. The use of flexible and lightweight fabrics and materials such as cotton, nylon, spandex and velcro stretch fabric and other suitable materials throughout the design of the enclosure 4 and the compression cover 6 improves patient comfort and compliance over prior art devices. The uniformity of the compressive force as applied against the surface area of the leg 50, and other body regions and parts, is also increased by the use of fabrics and materials as disclosed herein.

Referring to FIG. 3, a preferred embodiment of the invented system 80 that includes a circular enclosure 82 and a compression cover 84 is presented. The stitching 8 is again used to segregate the set of particles 16 into the subsets of particles 18 by means of forming a plurality of chevron shaped pockets 86 and a vertical stitch 88. The Chevron shaped pockets 86 are two inches in width and are intersected by the vertical stitch 88.

A plurality of straps 90 of the compression cover 84 each comprise a band of velcro loop-side fabric 92, a first end 94 and a second end 96. Each band 92 is two inches wide and six to forty inches long. Each first end 94 is attached to compression cover 84 at three inch intervals. Each second end 96 is fitted with a two inch by two inch square of velcro hook-side fabric 98.

A series of single looped rings 100 are attached to the compression cover 84 at three inch intervals. The straps 90 are passed through the rings 100 and are looped back so that the hook-side squares 98 can be attached to the velcro loop-side fabric bands 92. By this means and method compressive force is adjustably imparted to the enclosure 82.

The enclosure 82 and the compression cover 84 are optionally constructed from the same materials and fabrics as the enclosure 4 and the compression cover 6 of FIG. 1.

The chevron shaped pockets 86 with the vertical stitch 88 have been well used in treatment applications of secondary lymphedema, where it is advantageous to encourage lymphatic fluid out of a body area where the lymphatic system has been damaged and into other body areas where the lymphatic system is better functioning. Alternate pocket designs and orientations have been used with success in treating secondary lymphedema.

Figure 4:
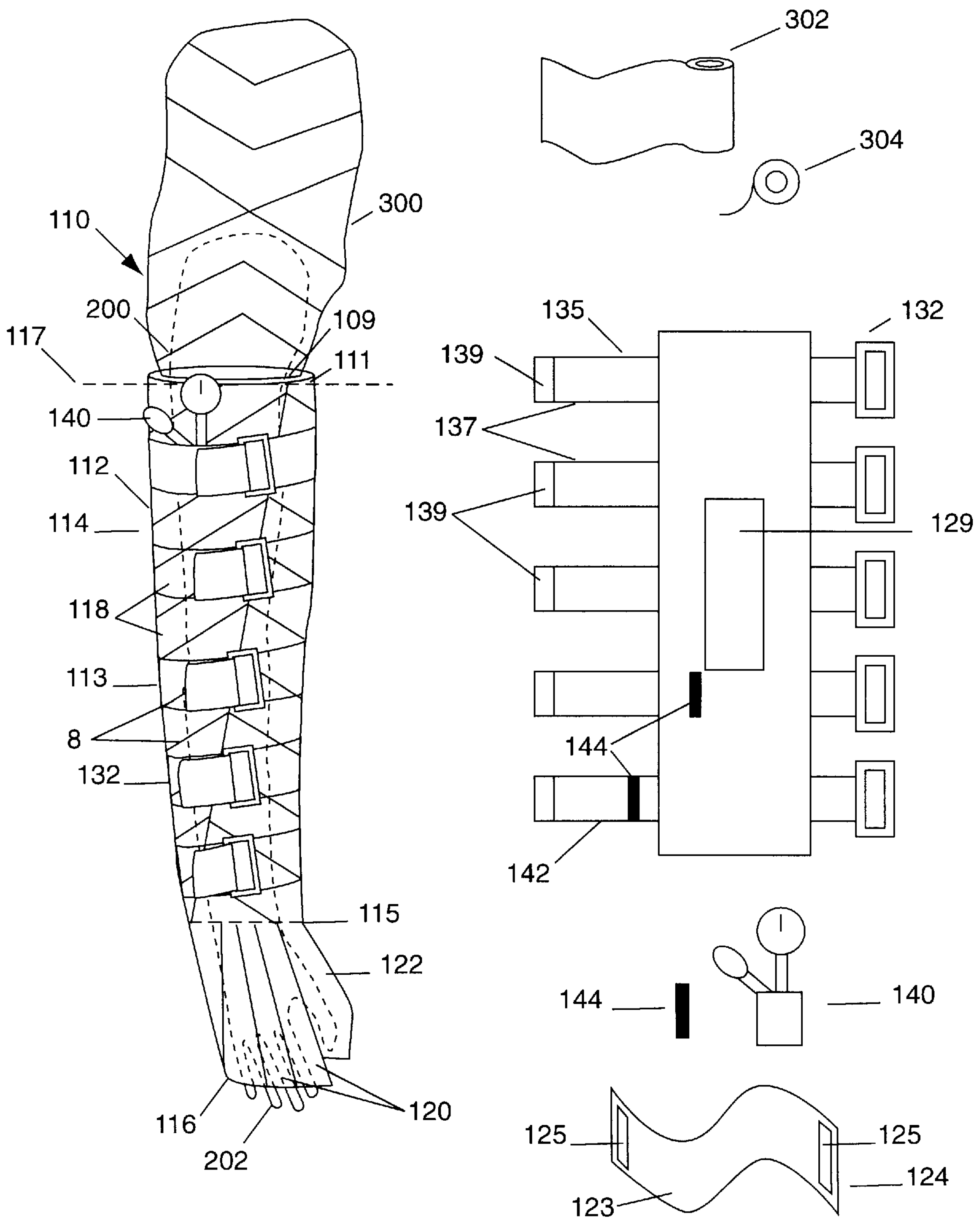
FIG. 4 shows a static reaction system designed for application against tissue swelling of shoulder, arm and hand. A directional flow pattern includes a plurality of chevron shaped pockets fitted together in the arm section of the enclosure. The chevron pockets of the arm section are oriented in a series pointing along a common axis, where the common axis travels from the inside distal region to the outside proximal region of the limb.

Referring now to FIG. 4, a static reaction system 110 with a directional flow pattern is illustrated. The system 110 of FIG. 4 is designed to provide therapeutic compression to an injured arm 200 and a hand 202 and includes an arm and hand enclosure 112, a compression cover 132 and a compression bandage 124. The enclosure 112 employs the stitching 8 to stitch the inner fabric sheet 109 and the outer fabric sheet 111 to contain the set of particles 16. The arm and hand enclosure 112 includes an arm section 114 and a hand section 116. A plurality of arm pockets 118 are located in the arm section 114 and a number of finger pockets 120 and a thumb pocket 122 are located in the hand section 116. The compressive means of system 110 comprises the compression cover 132 and the compression bandage 124. The compression cover 132 is used to press the arm section 114 against the arm 200 and the compression bandage 124 is used as compressive means to press the hand section 116 against the hand 202. Additional compression bandages 302, 304 may be applied to the patient's arm 200, as indicated by reference number 300.

The compression bandage 124 may be with a length of a loop velcro stretch fabric 123, such as Velstretch, in combination with an attached patch of velcro hook fabric 125, or other suitable compression bandaging materials known in the art.

The backing 133 of velcro loop fabric of the compression cover 132 presents a rectangular shape and may be effectively worn on either arm of a patient. A fabric section 129 comprises a four inch by six inch insert made of a flexible and pliant material, such as an elastic rubberized nylon stretch fabric, and allows the patient to more comfortably move an elbow through a full range of motion. The backing 133 presents velcro loop fabric on each of two sides. A plurality of straps 135 are each made with a velcro loop fabric strip 137 on each of two sides, and a velcro hook element 139. This configuration of straps 135, in combination with the two sides of velcro loop fabric 133, allows for easy repair of the invented system 110 if a hook element 139 is damaged or worn-out, in that an additional hook element can be sewn on to an alternate side of a strap 135, and the compression cover 132 can then be worn in reverse. The shape of the fabric section 129 is also designed to enable reversible application of the compression cover 132 on a left arm or a right arm, and with either side of the compression cover 132.

The arm section 114 is constructed to define a hollow tapered tubular cone shape 113, where the internal circumference of the enclosure 114 increases from a distal end 115 to a proximal end 117.

The enclosure 112 and the compression cover 132 are optionally constructed from the same materials and fabrics as the enclosures 4, 82 and the compression covers 6, 84 of FIGS. 1 and 3. The stitching 8 is employed in the invented system 110 of FIG. 4 to form a vertical stitch 130 and a plurality of pockets 118, 120, 122 and further to define the shape size and orientation of the plurality of pockets 118, 120, 122 in order to encourage the flow of interstitial fluid from the arm 200 and the hand 202 compressed by the invented system 110 of FIG. 4. The stitching 8 and the vertical stitch 130 are made of cotton thread, elastic thread or other suitable material.

The stitching 8 defines finger pockets 120 by stitching from points between adjacent fingers and knuckles and moving proximal towards the distal end 115 of the arm section.

The thumb pocket 122 contains more particles types 20, 22, 24 per surface area than the other pockets 118, 120 of the enclosure 114 and is therefore bulkier than these other pockets 118, 120. These extra particle types 20, 22, 24 are used to especially buffer and protect sensitive nerve structures located in the thumb web of the human hand.

The compression cover 132 is constructed from the same variety of materials as disclosed regarding the composition of the compression covers 6, 84 of FIGS. 1 and 3, but is designed to conform to the shape of the arm 200 and the arm enclosure 112 of FIG. 4. The compression bandage 128 is made of compression bandages, velcro fabric, velcro stretch fabric and/or other suitable materials known in the art and is wrapped around the hand section 116 in order to press the hand section 116 against the hand 202.

In certain alternate preferred embodiments of the present invention the compression cover 132 and the enclosure 112 or stitched together by the stitching 8 or otherwise molded or joined together by other suitable means known in the art.

In a recent trial, a preferred embodiment including an arm and hand section and a compressive cover similar to those of the static reaction system 110 was used to significantly alleviate swelling in a the arm of a 14 year old patient.

FIG. 4 further discloses a pressure gauge 140 and marking thread or adjustable velcro fabric element 144. Pressure gauge 140 is used by a medical practitioner to monitor the degree of pressure that the patient's arm 200 and hand 202 receive from the invented system 110 of FIG. 4 as the compression cover 132 and the compression bandage 128 is being tightened around the enclosure 112. Good results in interstitial drainage have been seen where the static pressure exerted by the present invention against a swollen body area is maintained below 35 mm of mercury.

In a clinical application, a qualified medical practitioner places the pressure gauge 140 between the arm 200 or the hand 202 and the enclosure 112 or the compression cover 132 and tightens the compression cover strap 142, while insuring that a desirable maximum pressure is not exceeded. The medical practitioner then locates the marking thread or adjustable velcro fabric element 144 on the compression cover 132 or the strap 135. The location of the marking thread or adjustable velcro fabric element 144 by a competent medical practitioner may allow the patient to thereafter safely self-administer and reattach the compression cover 132 to his or her arm 200, and thereby the arm section 114 of the invented system 110, by himself or herself at a later time and without the immediate assistance or supervision of a medical professional. Certain preferred embodiments of the invented system include colored thread or adjustable velcro fabric elements 144 for easy identification and color coding. The color coding can indicate the date or time of the most recent examination by a trained medical practitioner and/or the level of pressure desired.

Figure 4A:
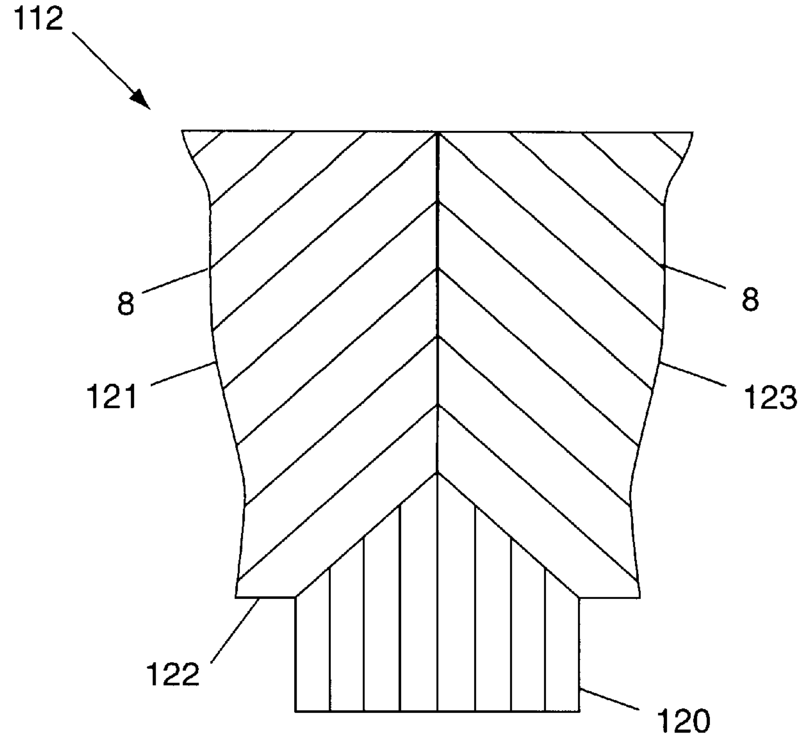
FIGS. 4*a* and 4*b* depict the arm and hand sections of the enclosure of FIG. 4 in two differing states of assembly.
Figure 4B:
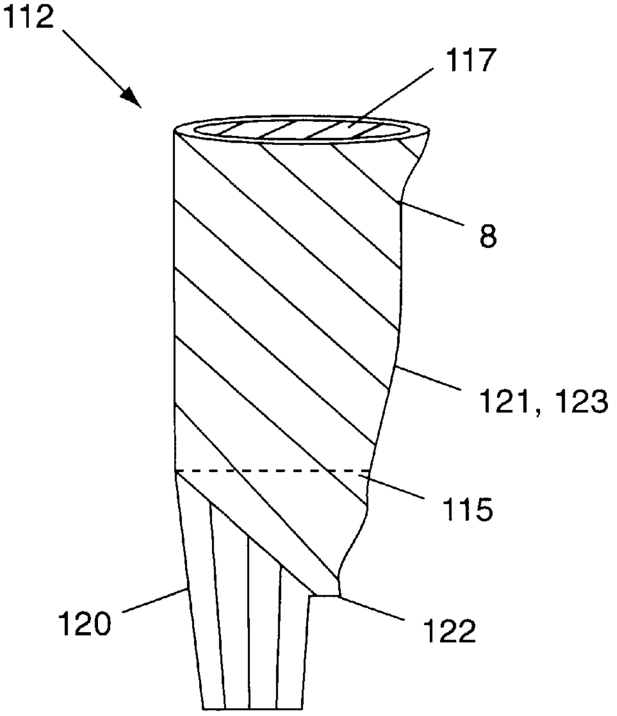

In reference now to FIGS. 4*a* and 4*b*, the enclosure 112 of FIG. 4 is shown in two states of manufacture. FIG. 4*a* shows the enclosure 112 as the two sheets of fabric 109, 111 enclosing particle types 20, 22, 24 and stitched together be the stitching 8. The stitching 8 is also used to define the vertical stitch 130, the arm pockets 118, the finger pockets 120 and the thumb pocket 122. FIG. 4*b* illustrates the enclosure 112 of FIG. 4 with additional the stitching 8 along a pair of seams 121, 123 and stitched together to form the enclosure 112 into a hollow tapered tubular cone shape.

Figure 5:
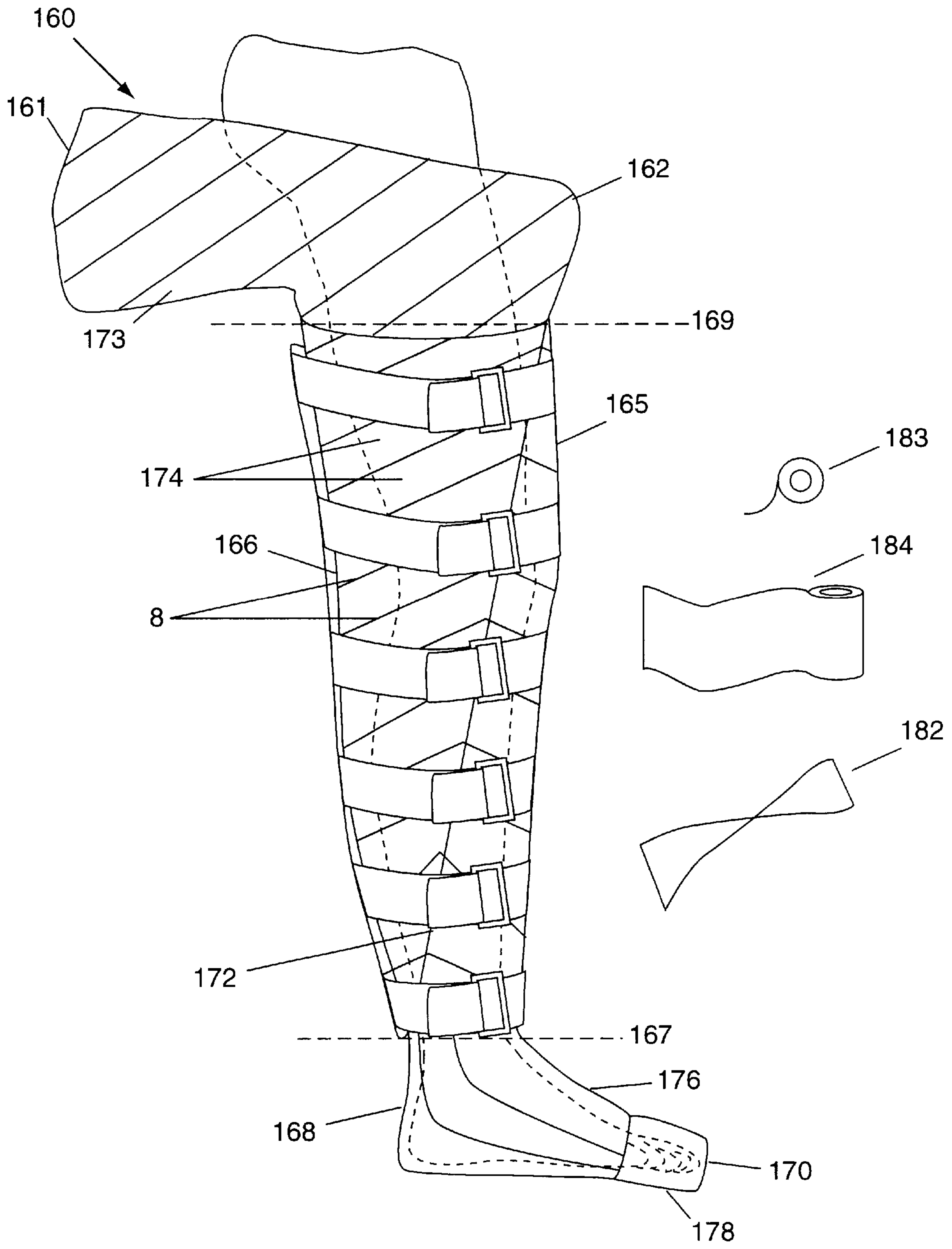
FIG. 5 illustrates a preferred embodiment of the invented system intended to treat a patient's hip, leg, foot and toes.

Referring now to FIG. 5, an alternate preferred embodiment of the invented system, a static reaction system 160, is shown to be designed to treat swelling, edema or lymphedema in a patient's hip, leg, foot and toes. The embodiment of the present invention of FIG. 5 includes an enclosure 162, a compression cover 164 and compression bandages 182, 183 and 184. The enclosure 162 contains a set of particles 16, as shown in FIG. 1, and includes a hip section 161, a leg section 166, a foot section 168 and a toe section 170. The leg section 166 is constructed to include a hollow tapered tubular cone shape 165, where the internal circumference of the enclosure 162 increases from a distal end 167 to a proximal end 169. The enclosure 162 may optionally be shaped such that the enclosure 162 is a reversible garment and may be used with either of two sides worn alternately as an outside or an inside.

The stitching 8 is used to form a vertical stitch 172, a plurality of hip chevron pockets 173, a plurality of leg chevron pockets 174, a plurality of foot pockets 176 and a toe pocket 178, whereby the set of particles 16 is divided into the separate subsets 18. The subsets 18 are contained by the vertical stitch 172 and within the various pockets 173, 174, 176 and 178. The size, shape and orientation of vertical stitch 172 the pockets 173, 174, 176 and 178 affect the rate at which interstitial fluid is evacuated from a body area. The use of the chevron shaped hip and leg pockets 173, 174 of widths of 2 inches have been used to good effect in reducing swelling. The alignment and configuration of the vertical stitch 172 and the plurality of leg chevron pockets 174 as shown in FIG. 5, i.e. where the points of the chevrons are oriented as pointing proximal and upwards, is also supportive of reducing tissue swelling.

The shape and positioning of the leg chevrons 174 draws the interstitial fluid in a pathway from the center inside of the leg and towards the outside and proximal end of the leg. It is of interest to note that Dr. J. R. Casley-Smith of Australia, Dr. Foldi of Germany and Dr. Vodder of Austria, three leading experts in lymphedema therapy, recommend that the preferred method of massaging lymphedemic patients consist of stroking from (1.) the center inside of a limb and (2.) proximal and towards the center outside of the limb.

The thinner, more pointed shape of the foot pockets 176 has also produced good results in reducing swelling in feet. The shapes and orientations of the foot pockets 176 as shown in FIG. 5 is additionally supportive of reducing tissue swelling in a foot.

The vertical stitch 172 is added to increase the rate at which an undesirable concentration of interstitial fluid is removed from a particular body area and returned to the circulatory system. The stitching 8 and the vertical stitch 172 may be made of cotton thread, elastic thread or other suitable material.

A toe section 170 includes the toe pocket 178, whereby a pocket of particle types 20, 22 and 24 can be placed around a patient's toes and toe joints.

The compression cover 164 of FIG. 5 may be constructed with velcro fabric, nylon, and/or other suitable fabrics known in the art. The compression cover 164 is shaped to provide compression against the full outside surface area of the leg section 166. The compression bandage 182 is wrapped around the foot section 168 and the toe section 170 to provide the required compression. The hip compression bandage 184 is used to compress and hold the hip section 161 against a patient's hip area. Both compression bandages 182, 184 are optionally made of compression bandaging, velcro fabric, velcro stretch fabric and/or other suitable materials known in the art.

An alternate preferred embodiment of the present invention which included a leg section and compressive cover similar in design to the leg section 166 and compressive cover 164 of the static reaction system 160 of FIG. 5 reduced the circumference of a mid-thigh of a middle aged patient from 46 inches to 39 inches within two weeks.

Figure 6:
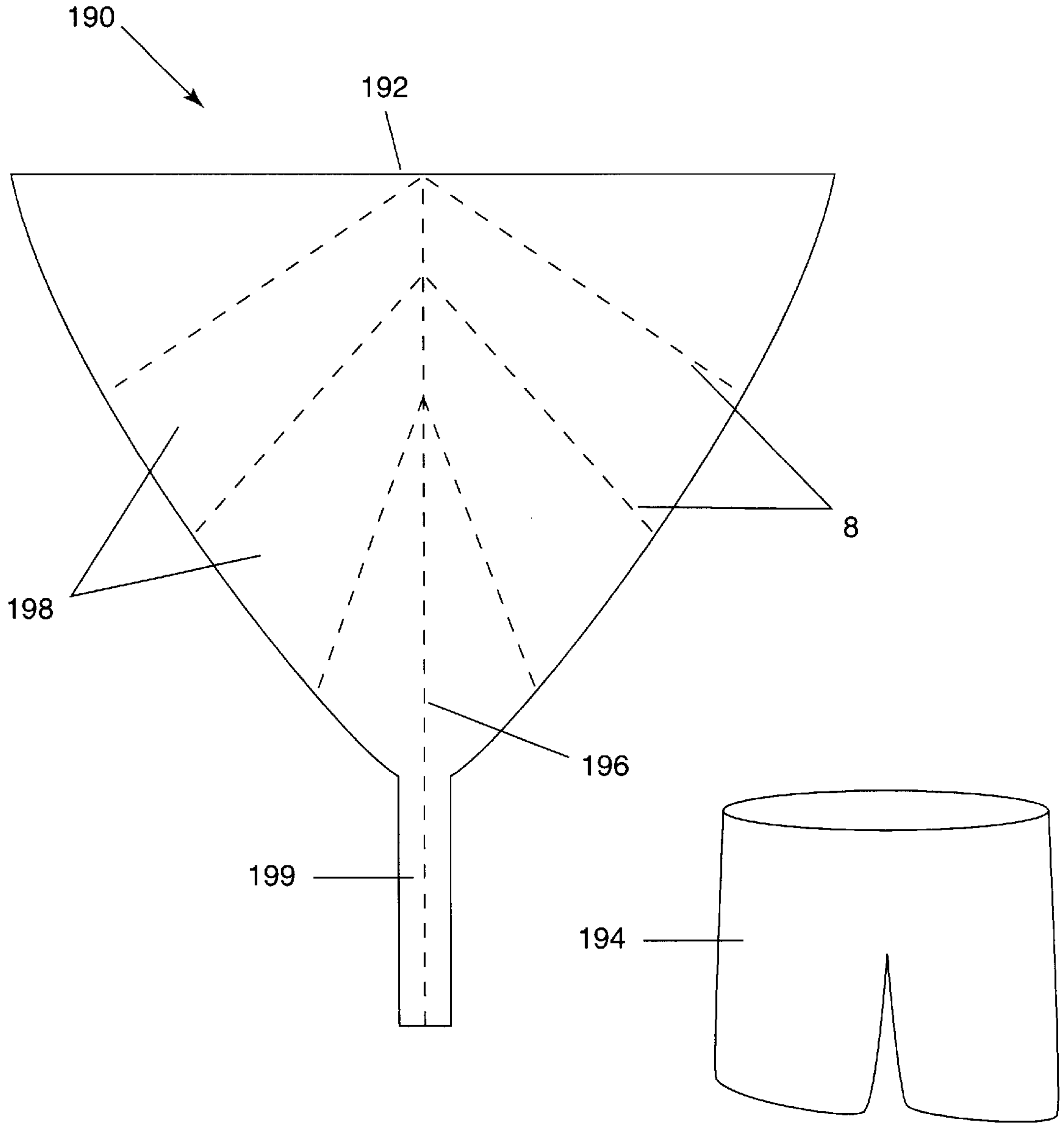
FIG. 6 presents a preferred embodiment of the invented system including an enclosure designed for use in treatment of swelling, edema or lymphedema of the lower abdomen, genitals and/or groin area.

Referring now to FIG. 6, a still alternate embodiment of the invented system 190 is shown which includes an enclosure 192 designed for use in treatment of swelling of the lower abdomen, genitals and/or groin, and with an elastic bicycle pants article 194 as a compressive means.

The stitching 8 is used to establish the vertical stitch 196, the chevron shaped pockets 198 and the groin pocket 199. The enclosure 192 of FIG. 6 is optionally made from the same set of fabrics and materials as the enclosure 4 of FIG. 1. The elastic bicycle pants article 194 is used by a patient to compress and hold the enclosure 192 against his or her lower abdomen, genitals and/or groin. The chevron shaped pockets 198 are pressed against the patient's lower abdomen and possibly genitals, and the groin pocket 199 is pressed up against the patient's groin and genitals.

Figure 7:
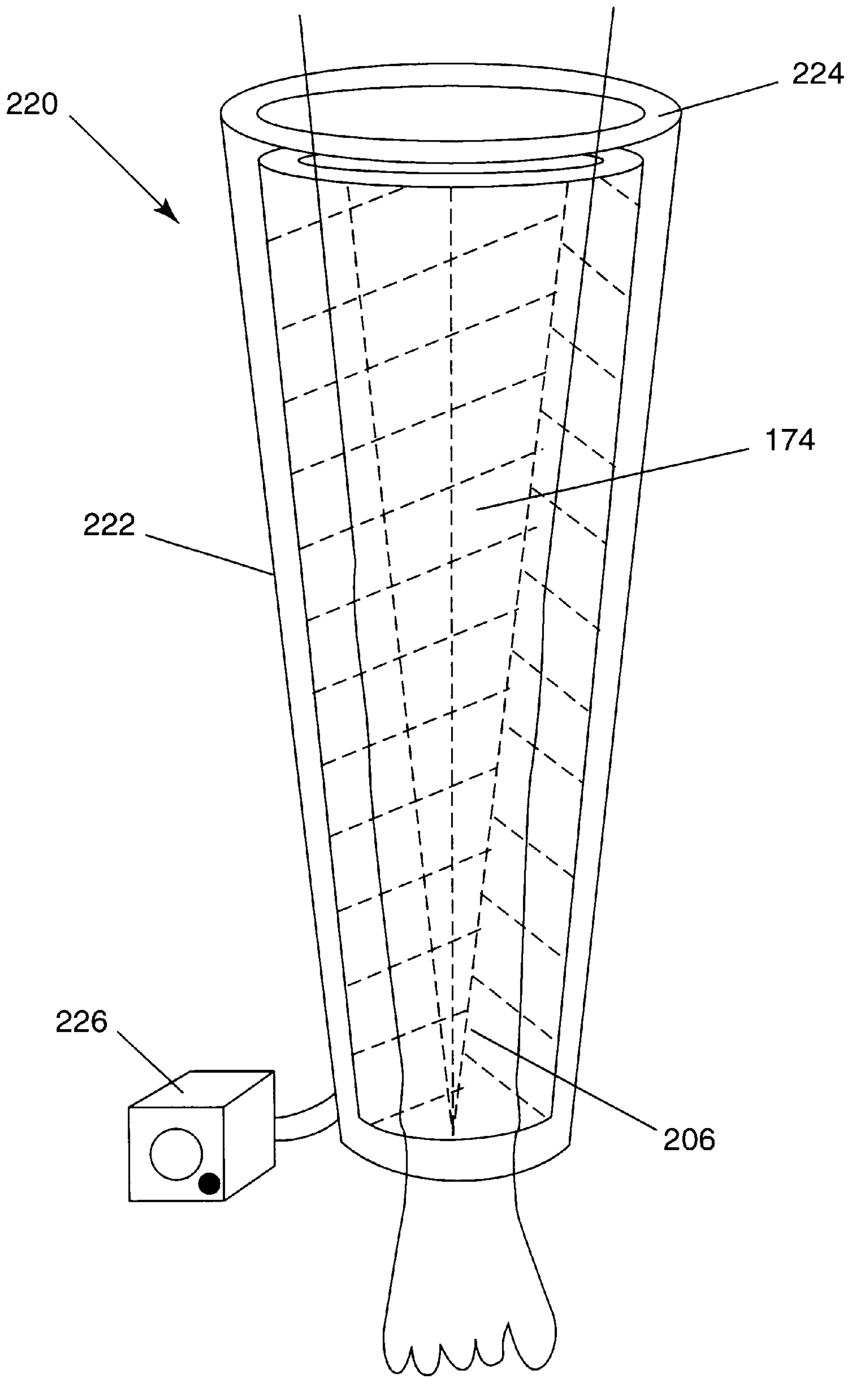
FIG. 7 presents a static reaction system which includes a pneumatic pressure pack.

Referring now to FIG. 7, a static reaction system 220 with a directional flow pattern is shown to include a leg enclosure 224, and a compressive means comprising a pneumatic pressure pack 222 and a pneumatic pump 226. The pressure pack 222 exerts an optionally constant or time varying pressure against the enclosure 224. The particle types 20, 22 and 24, as per FIG. 1, and the chevron leg pockets 174, as per FIG. 5, of the enclosure 224 are thereby pressed against the leg 206.

The pneumatic pressure pack 222 is optionally constructed with natural or synthetic rubber or other suitable materials and contains a pressurized gas or vapor. The pneumatic pressure pack 222 is inflated and deflated by means of the pump 226. The pump 226 is used to either maintain a constant static pressure in pressure pack 222 or to vary the pressure of pressure pack 222 over time.

Alternate embodiments of the pressure pack 222 further provide two or more individual pressure bladders that may be used to sequentially inflate and deflate in order to encourage interstitial fluid flow from leg 206 and into other areas of a patient's body.

Still another alternate embodiment of the present invention, known as a spiral compression wrap, comprises a relatively long enclosure with one or more pockets, where the pocket or pockets are shaped to extend along the length of the enclosure. Spiral compression wrap embodiments may be wrapped around a patient's limb and/or body area and compressed against the patient by compressive means such as a compression cover, compression bandages, pneumatic compression sources and other suitable compressive means known in the art. Certain spiral compression wrap embodiments may have enclosures of dimensions on the order of six to eight inches of width by several feet of length, whereby a wide range of patients and patient ailments may be comfortably and effectively treated. Best results to date have been achieved in spiral compression wrap embodiments with a quantity of four rectangular pockets shaped to extend along the length dimension of the spiral compression wrap enclosure.

Those skilled in the art will appreciate the various adaptations and modifications of the above described preferred embodiments which can be configured without departing from the scope and spirit of the invention. Therefore, it is understood that, within the scope of the appended claims, the invention may be practiced other than as specifically described herein.

We claim:

1. Apparatus for treating an elevated concentration of interstitial fluid in a body area of a patient, comprising:

an enclosure containing a multiplicity of resilient particles, said multiplicity of resilient particles being organized into a multiplicity of elongated pockets within said enclosure, said multiplicity of elongated pockets being separated from one another by a multiplicity of seams, said multiplicity of elongated pockets being organized in a chevron configuration defined by at least one vertical seam and a multiplicity of side seams intersecting said vertical seam, each of said multiplicity of side seams being angled distally away from where said side seams intersect said vertical seam; and a compression means for pressing said enclosure containing said multiplicity of resilient particles against the body area of the patient;

whereby said apparatus creates a directional flow pattern within the body area of the patient with each of said multiplicity of elongated pockets containing said multiplicity of resilient particles creating a high pressure area within the body area of the patient and each of said seams creating a low pressure flow channel adjacent to the high pressure areas, whereby fluid pressure in the high pressure areas urges interstitial fluid to flow from the high pressure areas into the low pressure flow channels, thereby providing a flow path for interstitial fluid to flow from the body area.

2. The apparatus of claim 1, wherein said compression means comprises an inflatable pressure bladder for pressing said enclosure containing said multiplicity of resilient particles against the body area of the patient.

3. The apparatus of claim 1, wherein said compression means comprises a compression cover that is separable from said enclosure containing said multiplicity of resilient particles.

4. The apparatus of claim 3, wherein said compression cover further comprises an elastic portion configured to be positioned over a bendable joint within the body area of the patient when said apparatus is attached to the body of the patient.

5. The apparatus of claim 3, wherein said compression cover further comprises a plurality of elastic straps having fasteners for fastening said compression cover around said enclosure containing said multiplicity of resilient particles.

6. The apparatus of claim 3, wherein said compression cover further comprises a plurality of elastic straps having fasteners for adjustably fastening said compression cover around said enclosure containing said multiplicity of resilient particles; and an adjustable marking element for marking each of said plurality of elastic straps to indicate a desired degree of compression.

7. The apparatus of claim 1, wherein said enclosure comprises an inner sheet and an outer sheet, and said seams are formed by attaching said inner sheet to said outer sheet of said enclosure to organize said multiplicity of resilient particles into said multiplicity of elongated pockets.

8. The apparatus of claim 7, wherein said seams are formed by stitching through said inner sheet to said outer sheet of said enclosure to organize said multiplicity of resilient particles into said multiplicity of elongated pockets.

9. The apparatus of claim 7, wherein said inner sheet and said outer sheet of said enclosure are made of a porous, breathable fabric.

10. The apparatus of claim 1, wherein said multiplicity of resilient particles are adhered to a surface of said enclosure.

11. The apparatus of claim 1, wherein said multiplicity of resilient particles comprises a mixture of resilient particles having a range of different sizes and a range of different resiliencies.

12. The apparatus of claim 1, wherein said enclosure is approximately circular in configuration.

13. The apparatus of claim 1, wherein said enclosure is approximately rectangular in configuration.

14. The apparatus of claim 1, wherein said enclosure is configured as a quadrilateral.

15. The apparatus of claim 1, wherein said enclosure has a tapered tubular configuration.

16. The apparatus of claim 1, wherein said enclosure is configured such that said vertical seam is oriented approximately parallel to an axis passing from distal to proximal through the body area of the patient.

17. Apparatus for treating an elevated concentration of interstitial fluid in a leg of a patient, comprising:

an enclosure containing a multiplicity of resilient particles, said multiplicity of resilient particles being organized into a multiplicity of elongated pockets within said enclosure, said multiplicity of elongated pockets being separated from one another by a multiplicity of seams, said multiplicity of elongated pockets being organized in a chevron configuration defined by at least one vertical seam oriented approximately parallel to an axis passing from distal to proximal through the leg of the patient and a multiplicity of side seams intersecting said vertical seam, each of said multiplicity of side seams being angled distally away from where said side seams intersect said vertical seam;

wherein said enclosure comprises a leg portion with a generally tapered tubular configuration to encircle the leg of the patient; and a compression means for pressing said leg portion of said enclosure containing said multiplicity of resilient particles against the leg of the patient;

whereby said apparatus creates a directional flow pattern within the leg of the patient with each of said multiplicity of elongated pockets containing said multiplicity of resilient particles creating a high pressure area within the leg of the patient and each of said seams creating a low pressure flow channel adjacent to the high pressure areas, whereby fluid pressure in the high pressure areas urges interstitial fluid to flow from the high pressure areas into the low pressure flow channels, thereby providing a flow path for interstitial fluid to flow from the leg of the patient.

18. The apparatus of claim 17, wherein said enclosure further comprises a foot portion having a multiplicity of elongated, resilient particle-containing pockets oriented approximately parallel to an axis passing from distal to proximal through the foot of the patient.

19. The apparatus of claim 18, wherein said enclosure further comprises a toe portion having at least one pocket containing a multiplicity of resilient particles.

20. The apparatus of claim 17, wherein said enclosure further comprises a hip portion having a multiplicity of elongated, resilient particle-containing pockets organized in a chevron configuration within said hip portion.

21. The apparatus of claim 17, wherein said enclosure further comprises:

a foot portion having a multiplicity of elongated, resilient particle-containing pockets oriented approximately parallel to an axis passing from distal to proximal through the foot of the patient; and a hip portion having a multiplicity of elongated, resilient particle-containing pockets organized in a chevron configuration within said hip portion.

22. Apparatus for treating an elevated concentration of interstitial fluid in an arm of a patient, comprising:

an enclosure containing a multiplicity of resilient particles, said multiplicity of resilient particles being organized into a multiplicity of elongated pockets within said enclosure, said multiplicity of elongated pockets being separated from one another by a multiplicity of seams, said multiplicity of elongated pockets being organized in a chevron configuration defined by at least one vertical seam oriented approximately parallel to an axis passing from distal to proximal through the arm of the patient and a multiplicity of side seams intersecting said vertical seam, each of said multiplicity of side seams being angled distally away from where said side seams intersect said vertical seam;

wherein said enclosure comprises an arm portion with a generally tapered tubular configuration to encircle the arm of the patient; and a compression means for pressing said arm portion of said enclosure containing said multiplicity of resilient particles against the arm of the patient;

whereby said apparatus creates a directional flow pattern within the arm of the patient with each of said multiplicity of elongated pockets containing said multiplicity of resilient particles creating a high pressure area within the arm of the patient and each of said seams creating a low pressure flow channel adjacent to the high pressure areas, whereby fluid pressure in the high pressure areas urges interstitial fluid to flow from the high pressure areas into the low pressure flow channels, thereby providing a flow path for interstitial fluid to flow from the arm of the patient.

23. The apparatus of claim 22, wherein said enclosure further comprises a hand portion having a multiplicity of elongated, resilient particle-containing pockets oriented approximately parallel to an axis passing from distal to proximal through the hand of the patient.

24. The apparatus of claim 23, wherein said hand portion of said enclosure further comprises individual finger pockets and a thumb pocket.

25. The apparatus of claim 22, wherein said enclosure further comprises a shoulder portion having a multiplicity of elongated, resilient particle-containing pockets organized in a chevron configuration within said shoulder portion.

26. The apparatus of claim 22, wherein said enclosure further comprises:

a hand portion having a multiplicity of elongated, resilient particle-containing pockets oriented approximately parallel to an axis passing from distal to proximal through the hand of the patient; and a shoulder portion having a multiplicity of elongated, resilient particle-containing pockets organized in a chevron configuration within said shoulder portion.

27. The apparatus of claim 22, wherein said compression means further comprises an elastic portion configured to be positioned over an elbow joint within the arm of the patient.

28. A method for treating an elevated concentration of interstitial fluid in a body area of a patient, comprising:

pressing an enclosure containing a multiplicity of resilient particles against the body area of the patient, said multiplicity of resilient particles being organized into a multiplicity of elongated pockets within said enclosure, said multiplicity of elongated pockets being separated from one another by a multiplicity of seams, said multiplicity of elongated pockets being organized in a chevron configuration defined by at least one vertical seam and a multiplicity of side seams intersecting said vertical seam, each of said multiplicity of side seams being angled distally away from where said side seams intersect said vertical seam;

creating a high pressure area within the body area of the patient with each of said multiplicity of elongated pockets containing said multiplicity of resilient particles, and creating a low pressure flow channel adjacent to the high pressure areas with each of said seams to urge interstitial fluid to flow from the high pressure areas into the low pressure flow channels; and conducting interstitial fluid from the body area through said low pressure flow channels.

29. The method of claim 28, wherein said enclosure is pressed against the body area of the patient by inflating an inflatable pressure bladder against said enclosure.

30. The method of claim 28, wherein said enclosure is pressed against the body area of the patient by a compression cover that is separable from said enclosure.

31. The method of claim 28, wherein said enclosure is pressed against the body area of the patient by a compression cover having an elastic portion positioned over a bendable joint within the body area of the patient.

32. The method of claim 28, wherein said enclosure is pressed against the body area of the patient by a compression cover having a plurality of straps with fasteners for fastening said compression cover around said enclosure.

33. The method of claim 28, further comprising marking at least one of said straps with an adjustable marking element to indicate a desired degree of compression.

34. The method of claim 28, wherein said enclosure is pressed against an arm of the patient.

35. The method of claim 28, wherein said enclosure is pressed against a leg of the patient.

* * * * *